United States Patent [19]
Adams

[11] Patent Number: 6,050,977
[45] Date of Patent: Apr. 18, 2000

[54] SYRINGE WITH RETRACTABLE NEEDLE ASSEMBLY

[75] Inventor: Robert D. Adams, Shamong, N.J.

[73] Assignee: Futura Medical Technologies Inc., Wilmington, Del.

[21] Appl. No.: 09/111,325

[22] Filed: Jul. 7, 1998

Related U.S. Application Data

[63] Continuation of application No. PCT/US97/20646, Nov. 14, 1997.

[51] Int. Cl.[7] .................................................... A61M 5/00
[52] U.S. Cl. ............................................ 604/195; 604/110
[58] Field of Search .................................. 604/195, 110, 604/198, 192, 263, 187

[56] References Cited

U.S. PATENT DOCUMENTS

| | | | |
|---|---|---|---|
| 4,820,278 | 4/1989 | Balisky | 604/218 |
| 4,838,869 | 6/1989 | Allard | 604/195 |
| 4,874,382 | 10/1989 | Lindemann et al. | 604/195 |
| 4,917,679 | 4/1990 | Kronner | 604/198 |
| 4,955,870 | 9/1990 | Ridderheim et al. | 604/195 |
| 5,120,310 | 6/1992 | Shaw | 604/110 |
| 5,188,613 | 2/1993 | Shaw | 604/195 |
| 5,190,526 | 3/1993 | Murray et al. | 604/110 |
| 5,209,739 | 5/1993 | Talalay | 604/195 |
| 5,267,961 | 12/1993 | Shaw | 604/110 |
| 5,320,606 | 6/1994 | Jore | 604/110 |
| 5,338,304 | 8/1994 | Adams | 604/110 |
| 5,385,551 | 1/1995 | Shaw | 604/110 |
| 5,389,076 | 2/1995 | Shaw | 604/110 |
| 5,395,337 | 3/1995 | Clemens et al. | 604/110 |
| 5,423,758 | 6/1995 | Shaw | 604/110 |
| 5,480,385 | 1/1996 | Thorne et al. | 604/110 |
| 5,656,031 | 8/1997 | Thorne et al. | 604/195 X |

FOREIGN PATENT DOCUMENTS

| | | |
|---|---|---|
| 0354824 | 2/1990 | European Pat. Off. . |
| 0480862 | 4/1992 | European Pat. Off. . |
| 0505330 | 9/1992 | European Pat. Off. . |
| 0704225 | 4/1996 | European Pat. Off. . |
| 2675999 | 11/1992 | France . |
| 9306880 | 4/1993 | WIPO . |
| 9511713 | 4/1995 | WIPO . |
| 9604030 | 2/1996 | WIPO . |

*Primary Examiner*—John D. Yasko
*Attorney, Agent, or Firm*—Volpe and Koenig, P.C.

[57] ABSTRACT

An improved syringe of the type having a hollow body which is closed at one end by an injection means and is open at the other end, the open end receives an elongated plunger means which moves through the hollow body and forces the contents of the body through the injection means. The improvement is comprised of an elastic member which retracts the injection means into a protective covering.

49 Claims, 14 Drawing Sheets

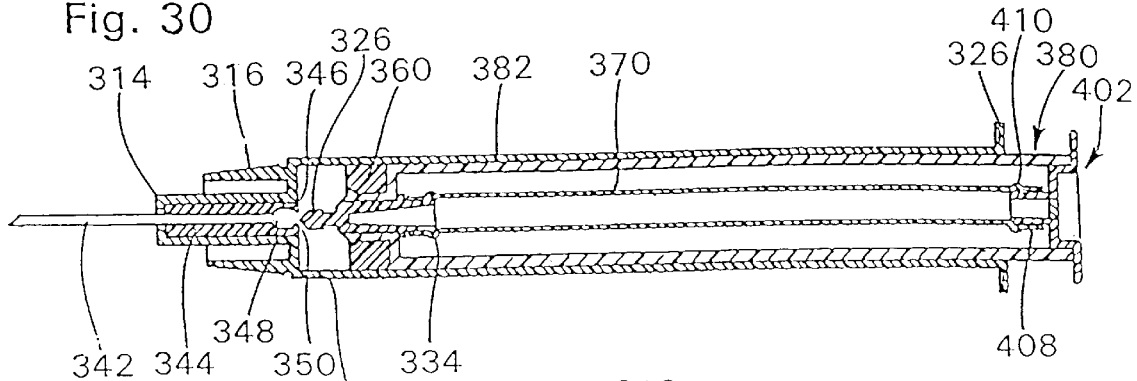
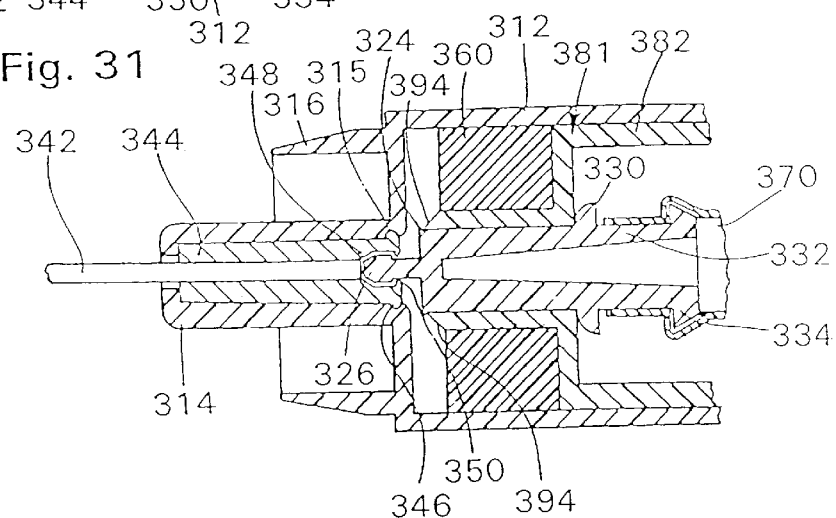
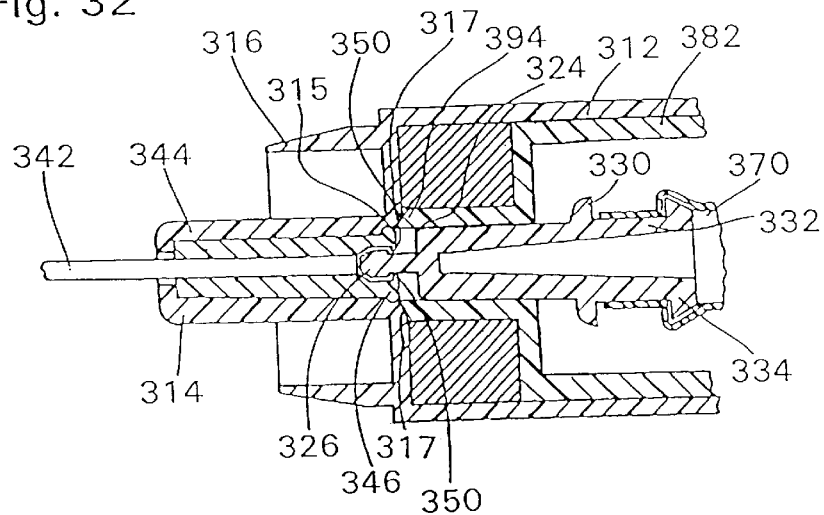

SYRINGE WITH RETRACTABLE NEEDLE ASSEMBLY

This is a continuation of International Application PCT/US97/20646 filed Nov. 14, 1997, which designated the United States and is now abandoned.

BACKGROUND OF THE INVENTION

1. Field of the Invention

The present invention relates generally to protection against an accidental sharps injury or stick from an unprotected needle. More particularly, the present invention relates to a retractable needle syringe for protection from an accidental sharps injury or stick from a used needle of the type commonly associated with medical practice. Most particularly, the present invention relates to an automatic retractable needle syringe for protection against an accidental sharps injury or stick from a used syringe.

2. Description of the Related Art

For some time, the art has recognized the desirability of protecting personnel from accidental sharps injuries or needle sticks. More recently, concerns have been expressed about the possibility of transmitting serious or potentially fatal infection as a result of such accidents. Most recently, the Occupation Safety and Health Administration has issued guidelines which are generally known as Standard 1910.1030. Although, the art has recognized the desirability of protecting against accidental sharps injuries or needle sticks, it is believed that practical protective devices are still not available.

U.S. Pat. No. 5,209,739 discloses a hypodermic needle assembly and a syringe, both having a retractable cannula. An elastomeric tube is connected between the cannula and the passage to the fluid chamber. In each of the embodiments, a separate mechanical device must be independently operated by the user to cause retraction of the cannula into a second compartment. Since the fluid must travel through the elastomeric tube to bypass the second compartment, there is a potential risk of injecting air directly into the patient if the elastomeric tube breaks.

European Patent No. 0 862 A1 discloses a device in which a needle is retracted into the syringe. In several of the embodiments, the device requires the user to independently operate a mechanical device to cause retraction of the needle. In the one embodiment which utilizes an elastic member, the elastic member is not preloaded and requires the user to depress the plunger to load the elastic member and thereafter continue to apply pressure on the plunger to avoid premature withdrawal of the plunger. As such, the device requires two hands for its operation.

U.S. Pat. Nos. 5,395,337, 5,267,961, 5,190,526, 4,955,870, 4,874,382 and 4,838,869 each disclose a device in which the needle is retracted by a compressive spring. In each of these devices, the spring and needle connection passes through the plunger sealing member. This results in complex sealing requirement for the plunger sealing member.

Accordingly, there is a need for a syringe having an automatically retracted used needle assembly that can be used in a conventional manner and does not require elaborate manufacturing or sealing means.

SUMMARY OF THE INVENTION

The present invention provides a disposable, single use syringe which has a hollow body that is substantially open at one end and is substantially closed at its other end except for an aperture through which an injection means passes. A retractable needle assembly is positioned within the hollow body so that the injection means passes out through the syringe body aperture. An elongated plunger, which moves in the hollow body for injection purpose, has a preloaded elastic member on spaced apart retainer means and means for retracting the needle assembly. Upon substantial completion of the injection, the preload on the elastic member is released and the relaxing elastic member draws the injection means in through the aperture.

BRIEF DESCRIPTION OF THE DRAWINGS

FIG. 30 depicts the syringe of FIG. 23 in an assembled but unused condition.

FIG. 31 depicts an expanded cross-sectional view of the forward portion of the syringe of FIG. 23 upon substantial depression of the plunger assembly.

FIG. 32 depicts an expanded cross-sectional view of the forward portion of the syringe shown in FIG. 23 immediately after complete depression of the plunger assembly.

DETAILED DESCRIPTION OF THE PREFERRED EMBODIMENTS

The preferred embodiments will be described with reference to drawing figures where the numerals represent like elements throughout.

Figure 1:
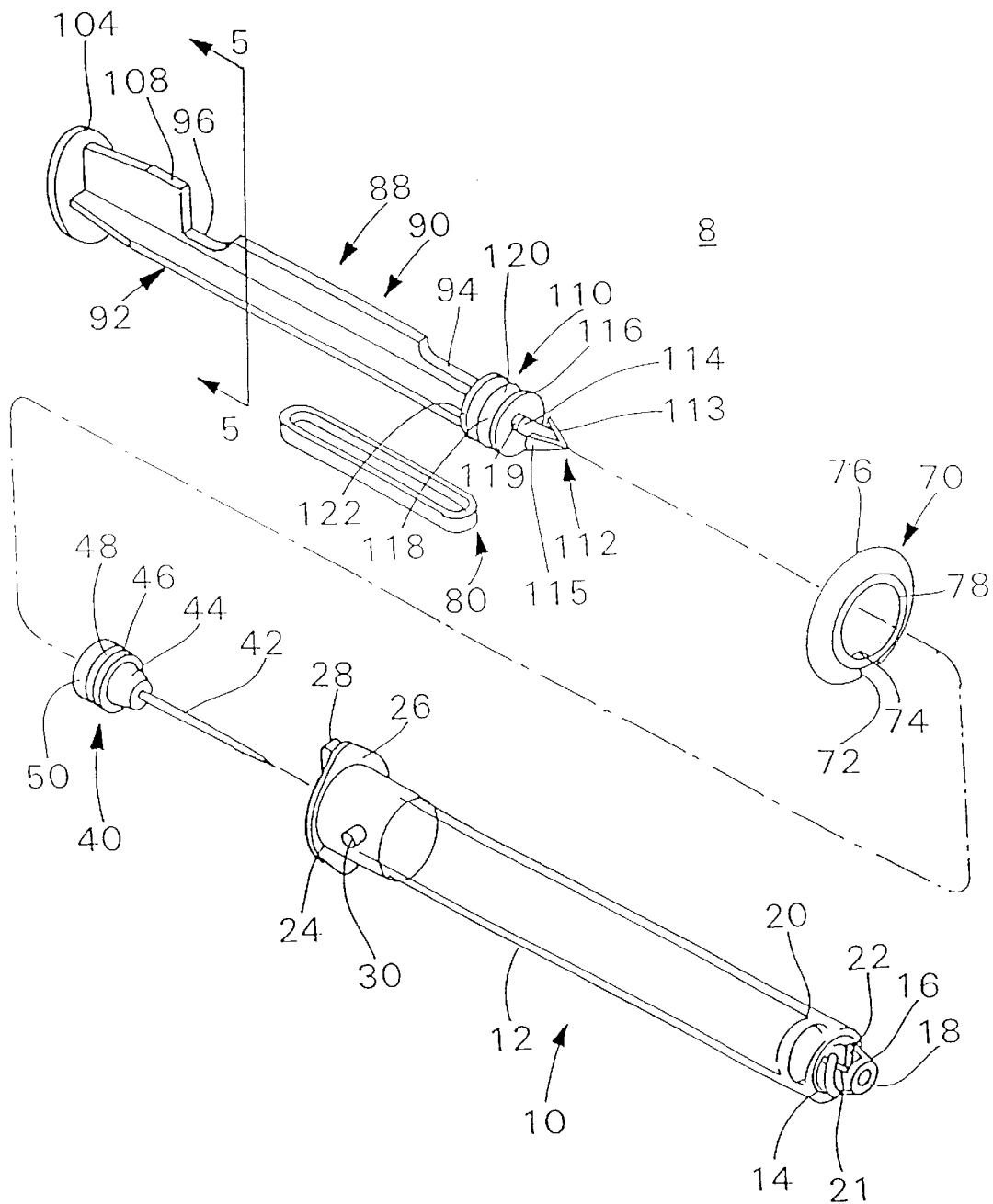
FIG. 1 is an exploded view of a syringe assembly in accordance with the present invention.

With reference to FIG. 1, the components of the first embodiment 8 of the invention will be described. The first embodiment 8 is comprised generally of the syringe 10, the needle assembly 40, the automatic release member 70, the elastic member 80 and the plunger assembly 88.

Figure 13:
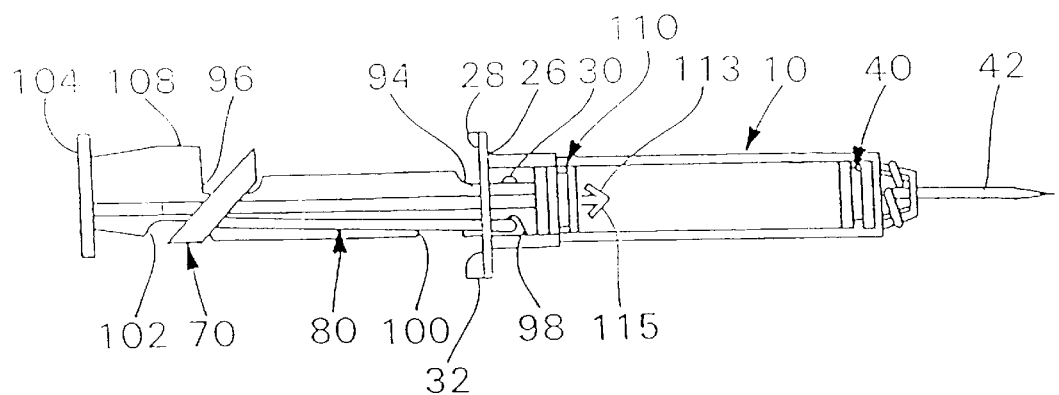
FIG. 13 depicts the syringe of FIG. 12 after the syringe has been rotated.

The syringe 10 is comprised of a hollow body portion 12 which has a closed end 14 and an open end 24 surrounded by a grip ring 26. Integral with grip ring 26 are a stop 28 and a guiding shoulder 32 which is shown in FIG. 13. On the interior of the hollow body 12, adjacent the open end 24, is a pin 30.

The closed end 14 is defined by a truncated cone 16 which includes a truncating plane having an aperture 18. On the interior of the hollow body 12, at a position adjacent to the closed end 14, is a retaining ring 20 that retains the needle assembly 40 in position during use. Alternatively, retaining ring 20 may be replaced by a plurality of projections.

The needle assembly 40 is comprised of a needle 42 which is centrally positioned in the conical projection 44. The conical projection 44 generally complements the interior of the truncated cone 16 in the syringe 10. However, the interior surface of the truncated cone 16 has a number of ridges 21 which extend from the closed end 14 to the truncating plane of the cone 16. These ridges 21 act to simplify the breaking of the seal between the needle assembly 40 and the interior surface of cone 16, thereby reducing the resistance which must be overcome to withdraw the needle assembly 40.

Figure 2:
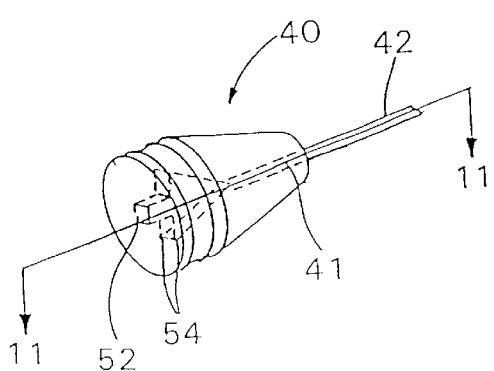
FIG. 2 depicts the needle assembly.

Immediately adjacent to the projection 44 is a resilient collar 46. Immediately behind the collar 46 is the angular recess 48. Adjacent to the recess 48 is the sealing ring 50. The resilient collar 46, the angular recess 48 and the sealing ring 50 are all formed as a unitary molding of synthetic rubber. The interior recess 41 of needle assembly 40 communicates with the hollow needle 42. Along the rear surface of the needle assembly is a rectangularly configured cavity 52 which is shown in detail in FIG. 2. In the preferred embodiment, the cavity 52 is shaped like an arrow head with narrowly spaced walls 54 defining the shorter side of the rectangle.

Automatic release member 70 holds the elastic member 80 on the plunger member 88 in a preloaded or tensioned condition until the plunger member 88 is completely depressed. In the preferred embodiment, the elastic member 80 is an elastic band which is approved for medical uses. The plunger assembly 88, the elastic member 80, and the automatic release 70 will be described in greater detail with reference to FIGS. 3–7.

Figure 3:
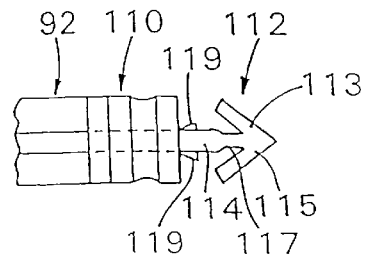
FIG. 3 depicts the tip end of the plunger assembly.

The plunger assembly 88 includes a plunger portion 90 and a sealing member 110. The plunger portion 90 has a shaft 92 which terminates at one end in the force application pad 104 and at its other end in geometrically configured tip 112. As shown in FIG. 3, geometrically configured tip 112 is arrow shaped with two collapsible fins 113, 115 as rod 114 extends from the end of the shaft 92. At the tip of rod 114 are detents 117 which allow each fin 113, 115 to collapse against the rod 114. The base of rod 114 has two ramps 119 which assist in withdrawing tip 112 from the needle assembly cavity 52 which is in its initial position. A sealing member 110 is placed on the rod 114 in sealing engagement therewith. A suitable sealing member 110 is described in detail in my U.S. Pat. No. 5,338,304, which description is incorporated herein by reference.

Figure 4:
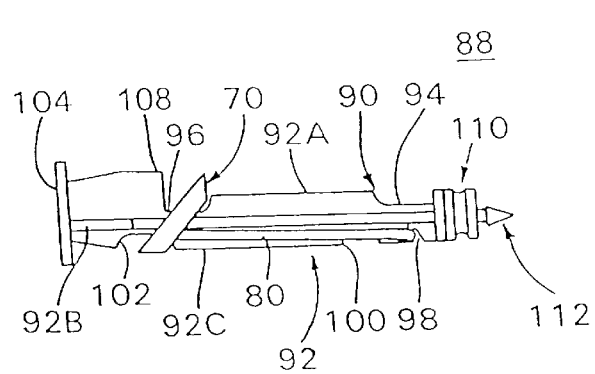
FIG. 4 is a side elevation of the plunger assembly.
Figure 5:
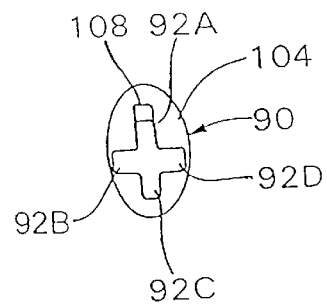
FIG. 5 is a cross sectional view of the plunger assembly taken along line 5—5 of FIG. 1.

As shown in FIGS. 4–5, the shaft 92 consists of 4 ribs 92A, 92B, 92C, 92D formed in a substantially cross shape with angular channels formed between adjacent ribs. The upper rib 92A has a rotation notch 94 adjacent the sealing member 110 and a first retaining notch 106 adjacent the force applicator pad 104. The lower rib 92C has a second retaining notch 102 adjacent the force applicator pad 104, a third retaining notch 98 adjacent the sealing member 110, and a locking notch 100 therebetween.

The automatic release member 70 is placed on the plunger shaft 92 with its upper portion located in the first retaining notch 96 and its lower portion in the second retaining notch 102. The elastic member 80 is attached at one end to the automatic release member 70 and at the other end to the third retaining notch 98. The second retaining notch 102 and the third retaining notch 98 are spaced so that the elastic member 80 is preloaded, i.e. there is tension in the elastic member 80. The automatic release member 70 is held in the second retaining notch 102 by the tensioned elastic member 80. When the lower portion of the automatic release member 70 is held in the second retaining notch 102, the upper portion is at an approximately 45 degree angle from the lower portion and is unrestrained in the first retaining notch 96.

Figure 6:
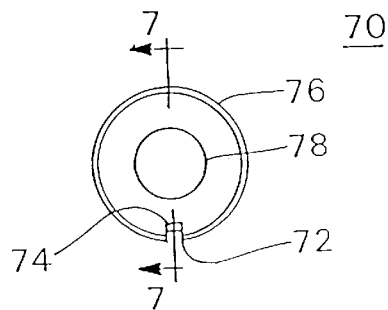
FIG. 6 is a front elevational view of the automatic release member.
Figure 7:
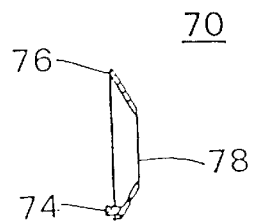
FIG. 7 is a cross sectional view of the automatic release member taken along line 7—7 of FIG. 6.

As shown in FIGS. 6 and 7, the automatic release member 70 is generally a beveled ring. The small opening 78 is large enough to allow the automatic release member 70 to pass along the plunger assembly 88 until it reaches the trailing edge 108 of the first retaining notch 96. The trailing edge 108 fits into the large opening 76, but will not pass through the small opening 78. The lower portion of the automatic release member 70 has a notch 72 and a projection 74. The elastic member 80 is passed through notch 72 and is hooked or secured to the projection 74. The automatic release member 70 is then positioned on the plunger assembly 88 as previously described above.

Figure 8:
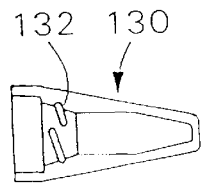
FIG. 8 shows a side elevation of a protective cap which may be used with the syringe.
Figure 9:
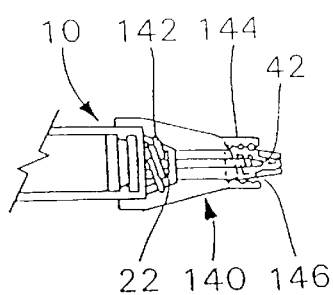
FIG. 9 depicts a Luer-lock adapter attached to the syringe.

FIG. 8 shows a protective cap 130 with threads 132 which may be used with the device 8. In the preferred embodiment, the exterior surface of truncated cone 16 has threads 22 which allow the syringe 10 to be connected to the threaded cap 130 and other equipment which uses a standard Luer-lock connection. FIG. 9 shows a Luer-lock adapter 140 with threads 142 which mate with the threads 22 on the syringe 10. The opposite end of the adapter 140 has a second set of threads 144 and a membrane 146 which covers the end of the adapter 140 to keep it sanitary. To utilize the device 8 with an intravenous line, the adapter 140 is connected to the closed end 14 of the syringe 10. As the adapter 140 is connected to the syringe 10, the needle 42 punctures the membrane 146 and extends slightly past the end of the adapter 140. The second set of threads 144 can than be used to connect the device to an intravenous line. Apart from connection to a Luer-lock rather then direct injection into the patient, the device 8 operates as described hereinafter.

Having described the components of the first embodiment 8, its operation will be described in more detail with reference to FIGS. 10–20.

Figure 10:
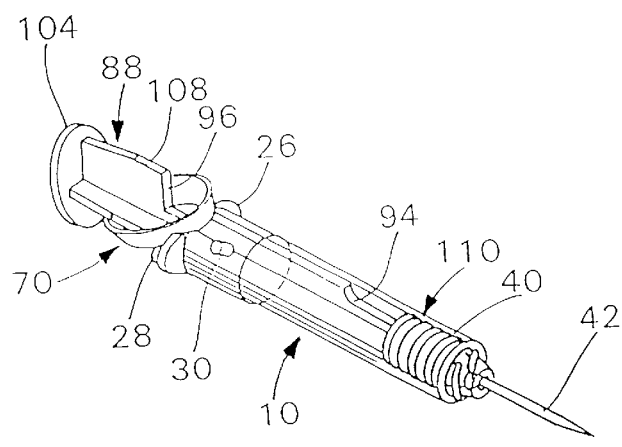
FIG. 10 depicts the syringe of FIG. 1 in an assembled but unused condition.
Figure 11:
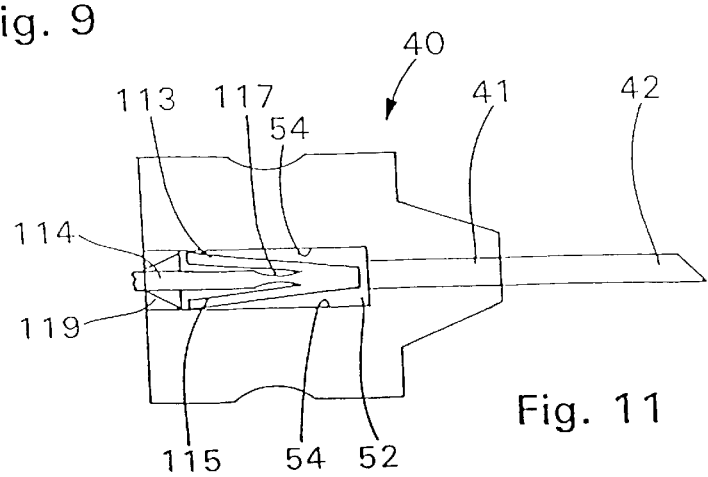
FIG. 11 is an expanded view of the cross section of the needle assembly taken along line 11—11 of FIG. 2, with the tip of the plunger inserted therein.

FIG. 10 shows the device 8 when it is first removed from its packaging and the protective cap 130 is removed. The plunger assembly 88 is aligned within the syringe 10 such that the pin 30 is positioned in the groove between the upper rib 92A and the left rib 92B. The plunger assembly 88 is in a first alignment in which the fins 113, 115 are horizontal and therefore are collapsed by the vertical walls 54 of the cavity 52 as shown in FIG. 11. This alignment keeps the tip 112 from locking with the needle assembly 40. The ramps 119 help prevent the collapsed fins 113, 115 from catching on the walls 54 of the cavity.

Figure 12:
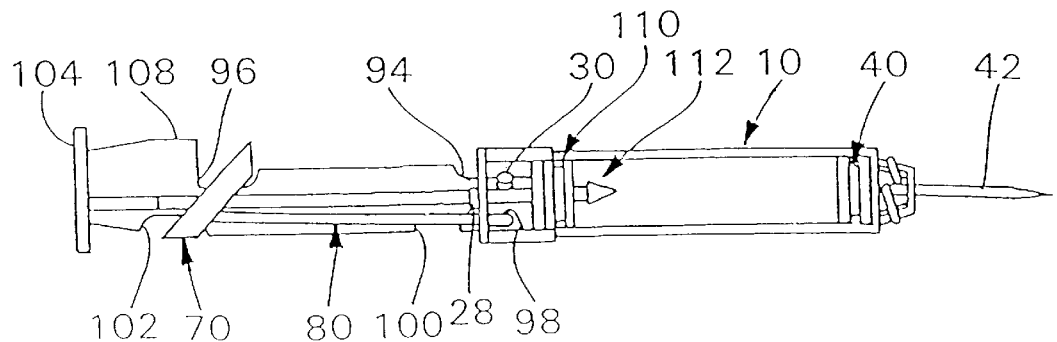
FIG. 12 depicts the syringe of FIG. 10 after the plunger assembly has been withdrawn.

The plunger assembly 88 is then withdrawn to the position shown in FIG. 12 to fill the hollow body 12 in a conventional manner. It will be noted that in the withdrawn position, the elastic member 80 remains in a preloaded position. Since the elastic member 80 is tensioned between two points on the plunger, the elastic member 80 does not act to withdraw or depress the plunger assembly 88. With the plunger assembly 88 withdrawn sufficiently, the pin 30 is aligned with the rotation notch 94. As shown in FIG. 13, syringe 10 and plunger assembly 88 can then be rotated relative to each other so that the fins 113, 115 are in alignment with the narrowly spaced walls 54 of the cavity 52.

Once the air has been purged from the syringe 10 in a known manner, the device 8 is ready for injection of the needle 42 into the patient. As stated above, the elastic member 80 is not acting to move the plunger assembly 88 in either direction. Therefore, the user is free to hold the device 8 in the traditional dart like fashion between their thumb and forefinger of one hand, and use the other hand to pinch the patient's skin at the point of insertion for subcutaneous injection, spread the skin for intermuscular injection, and stabilize the skin for IV injection. These methods of injection are the generally preferred methods in the medical field. Once the user has inserted the needle 42 into the patient, the user injects the substance into the patient by depressing the force application pad 104.

Figure 14:
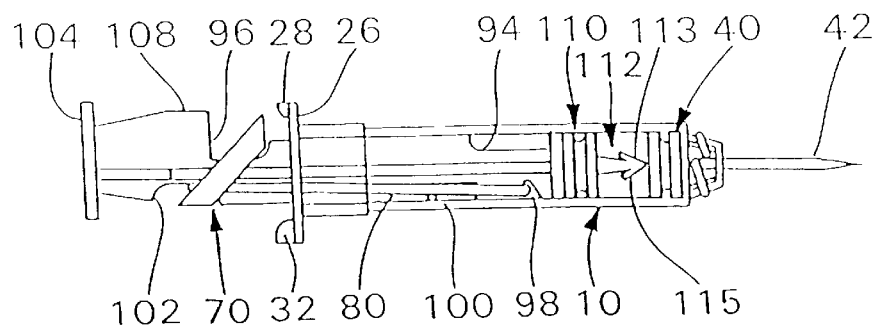
FIG. 14 depicts the syringe of FIG. 13 as the sealing member begins to connect with the needle assembly.

As shown in FIG. 14, as the geometrically configured tip 112 begins to pass into the needle assembly 40, the upper portion of the automatic release member 70 is about to contact the finger grip 26 and the stop 28. Slightly thereafter, the upper portion of the automatic release member 70 contacts the finger grip 26 and the stop 28 and begins to move upward on the stop 28 as shown in FIG. 15.

Figure 15:
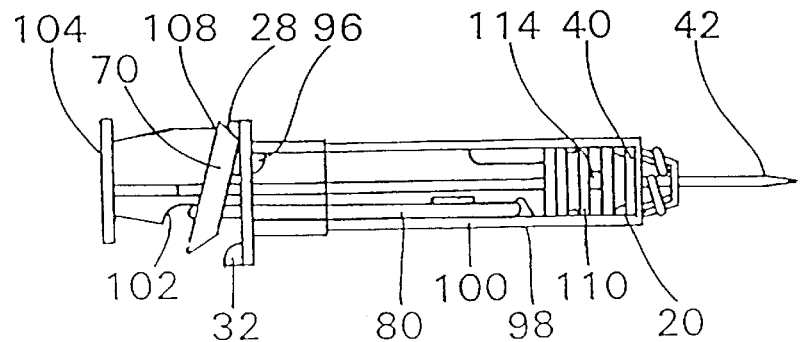
FIG. 15 depicts the syringe of FIG. 14 upon substantial depression of the plunger assembly.
Figure 16:
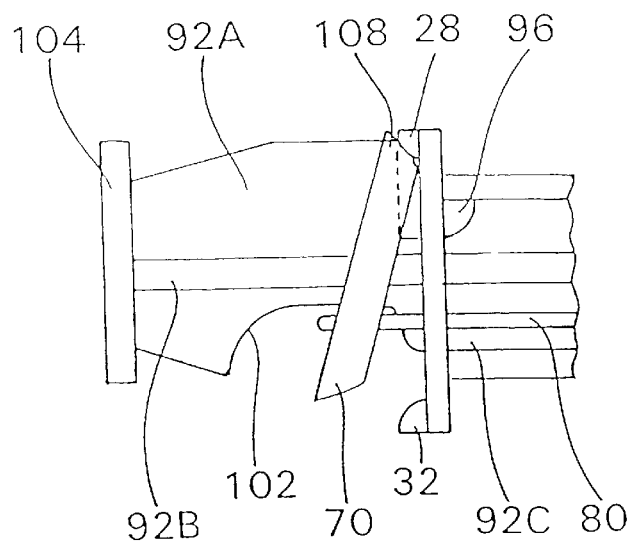
FIG. 16 depicts an expanded view of the rear portion of the syringe shown in FIG. 15.

FIG. 16, which is an expanded view of the rear of the device 8 in the position of FIG. 15, shows the trailing edge 108 of the first retaining notch 96 pinching the automatic release member 70 between itself and the stop 28. The continuing force as the plunger assembly 88 is completely depressed and the pinching of the automatic release member 70 between the trailing edge 108 and the stop 28 causes the lower portion of the automatic release member 70 to move down and backward, thereby automatically releasing from the second retaining notch 102 as depression of the plunger assembly 88 is completed.

Figure 17:
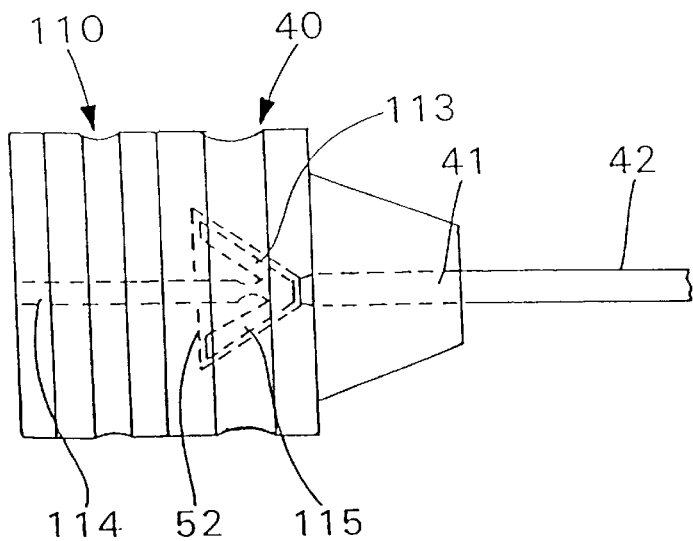
FIG. 17 depicts an expanded view of the mated needle assembly and plunger tip of FIG. 16.

As explained earlier, the fins 113, 115 of the tip 112 are now aligned with the longer sides of the rectangular cavity 52. The fins 113, 115 collapse as the tip 112 passes into the cavity 52, but upon complete depression of the plunger assembly 88, open inside the cavity 52 as shown in FIG. 17, thereby locking the plunger assembly together with the needle assembly 40. The notch 96 in plunger assembly 88 is of sufficient length so plunger 88 can be depressed slightly further to account for any possible compression between the needle assembly 40 and the sealing member 110 and to ensure that the components mate and that all of the fluid has been discharged from the syringe 10.

Figure 18:
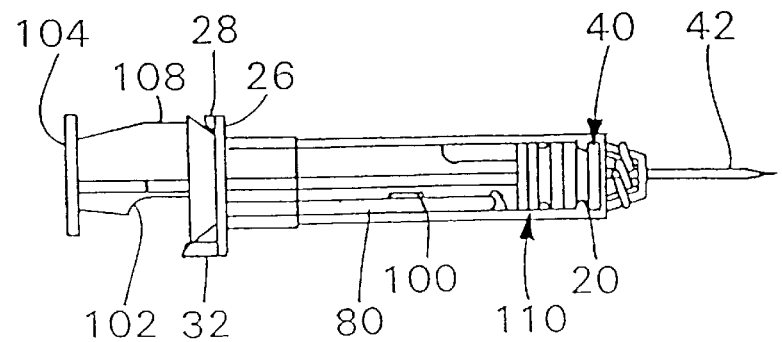
FIG. 18 depicts the syringe of FIG. 16 immediately after complete depression of the plunger assembly.
Figure 19:
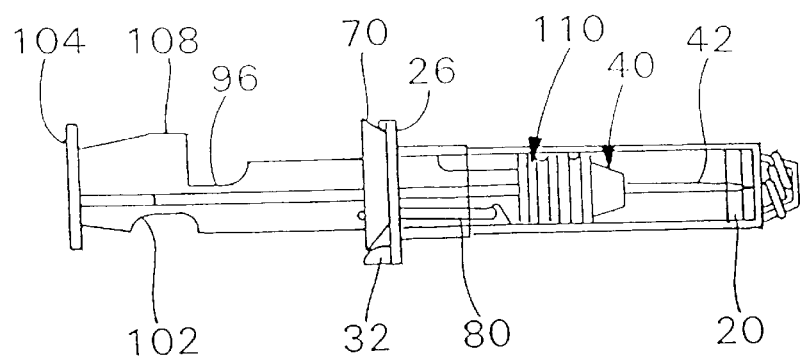
FIG. 19 depicts the syringe of FIG. 18 after it has been used and the needle has been retracted.
Figure 20:
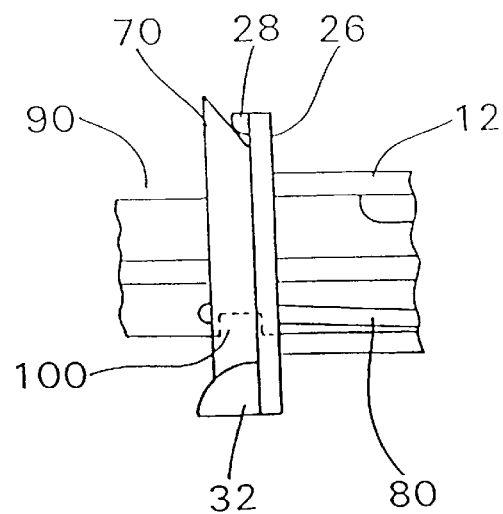
FIG. 20 depicts an expanded view of the rear portion of the syringe shown in FIG. 12.

As the automatic release member 70 releases, the plunger assembly 88 recoils slightly and guiding shoulder 32 urges the automatic release member 70 upward until it sits against the open end 14 of the syringe and the grip ring 26 as shown is FIG. 18. Since the elastic member 80 is now tensioned between a forward point on the plunger assembly 88, and a fixed point which is separate from the plunger assembly 88 and rear of the first point, the elastic member 80 retracts the plunger assembly 88 until the entire needle 42 is retracted within the syringe 10 as shown in FIG. 19. Once the plunger assembly 88 has been completely retracted, the guiding shoulder 32 continues to urge the automatic release member 70 inwardly until it locks into locking notch 100 as shown in FIG. 20. At this point, the plunger assembly 88 is secured so that it cannot be accidentally withdrawn from the syringe 10 or pushed so the needle projects from the syringe and so that the device 8 cannot be reused.

Figure 21:
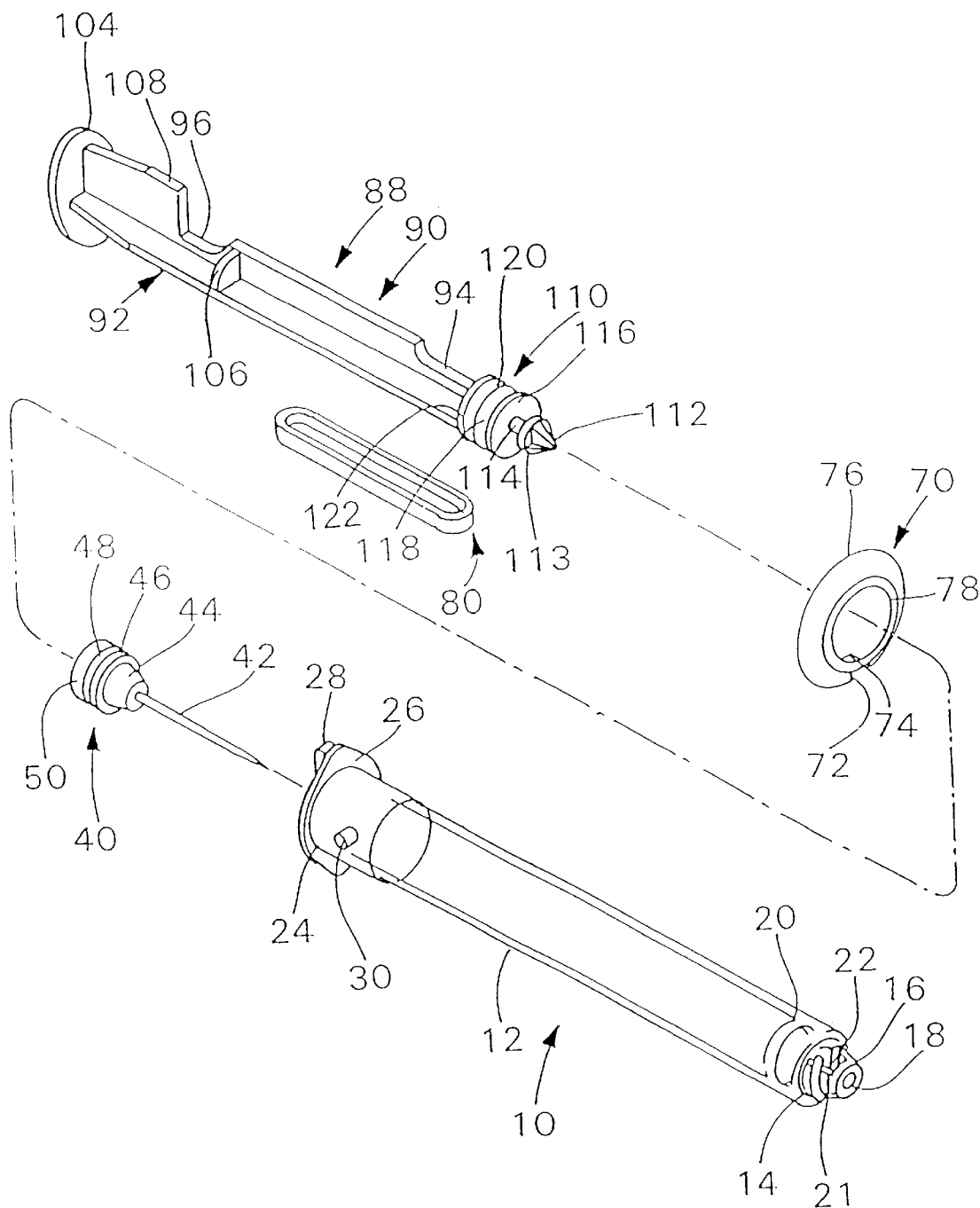
FIG. 21 is an exploded view of a second embodiment of the present invention.
Figure 22:
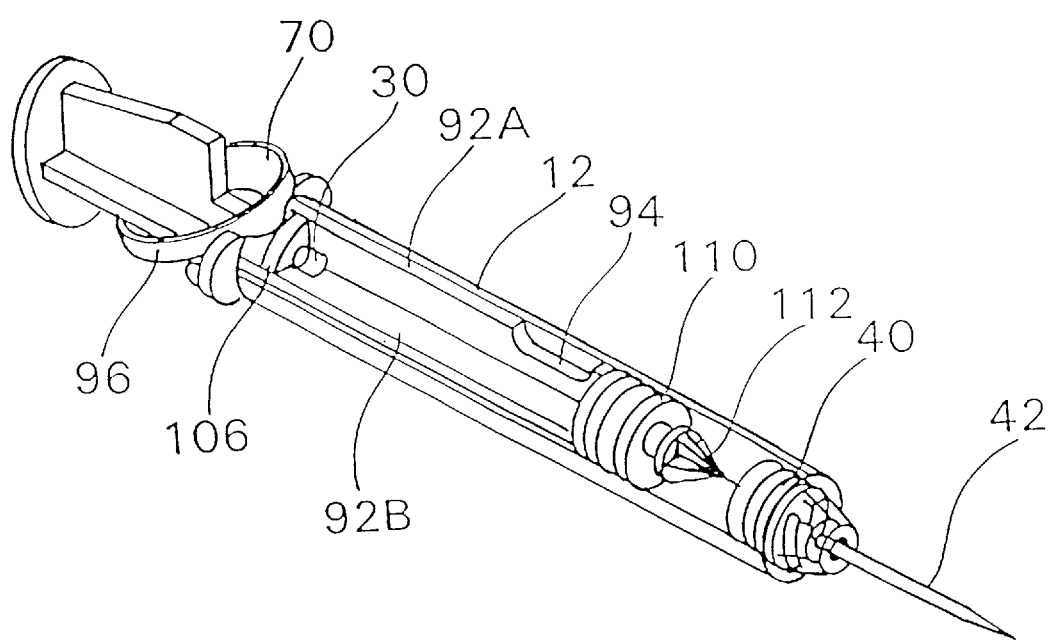
FIG. 22 depicts the syringe of FIG. 21 in an assembled but unused condition.
Figure 23:
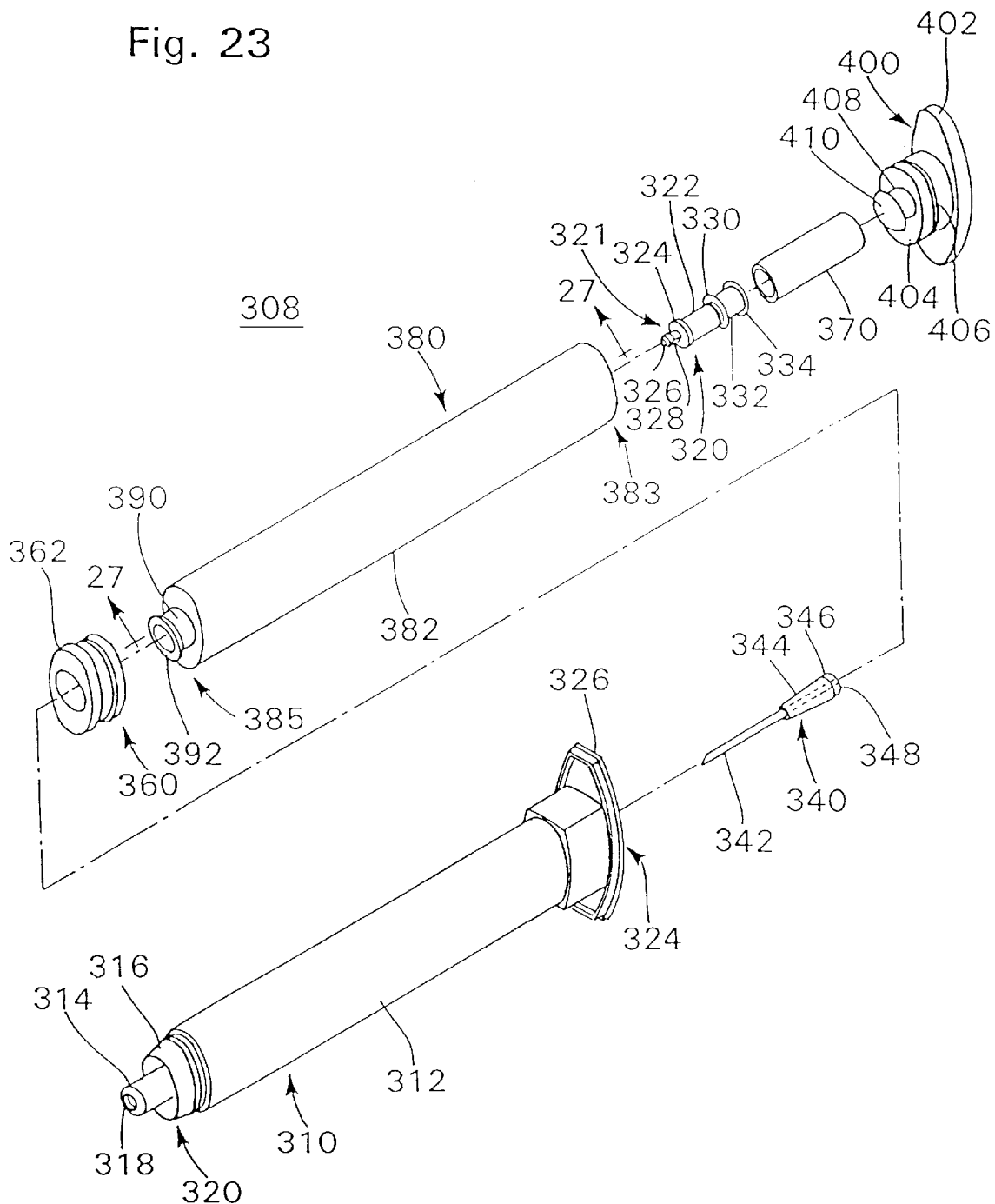
FIG. 23 is an exploded view of a third embodiment of the present invention.

Now with reference to FIGS. 21–22, a second embodiment of the device 208 will be described. The components of the device 208 are generally the same as in the first embodiment, however, the tip 112 and cavity 52 have different configurations, and there is an abutment 106 formed between upper rib 92A and left rib 92B. The tip 112 is configured to have a plurality of fins 213 or alternatively, is shaped as a hemisphere as described in my earlier referenced U.S. Pat. No. 5,338,304, which description is incorporated herein by reference. The cavity 52 is shaped to compliment each tip 112 configuration respectively.

Operation of the device 208, is generally the same as operation of the first embodiment. However, since the tip 112 does not have a locking and a non-locking alignment, abutment 106 is provided to prevent premature mating of the plunger tip 112 and the cavity 52. As shown in FIG. 22, the plunger is initially aligned in the syringe such that abutment 106 contacts the pin 30, thereby preventing complete depression of the plunger assembly 88 and premature meeting of the tip 112 and the needle assembly 40. The device is then filled as in the first embodiment. The syringe is then again rotated such that the pin 30 passes through notch 94 until the pin 30 is aligned in the groove between upper rib 92A and right rib 92D. Since there is no abutment in this groove, the syringe can now be completely depressed. As the device 8 in the first embodiment is rotated in the same manner, an abutment 106 could be included in the first embodiment between upper rib 92A and left rib 92B to ensure that the tip 112 and needle assembly 40 do not prematurely mate.

Operation of the automatic release member 70 and retraction of the needle assembly 40 then proceeds as described for the first embodiment.

Now with reference to FIGS. 23–33, a third embodiment of the device 308 will be described. The third embodiment 308 is comprised generally of the syringe 310, the needle assembly 340, the elastic member 370, and the plunger assembly 380.

Figure 26:
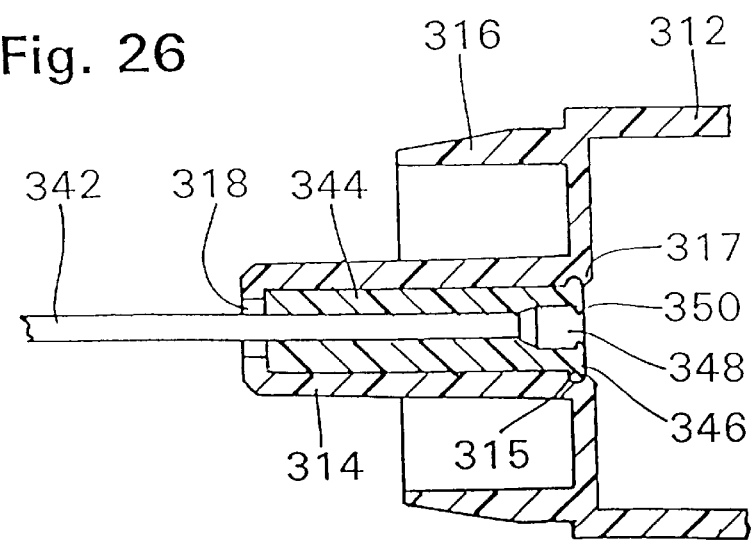
FIG. 26 is an expanded cross-sectional view of the forward portion of the syringe hollow body of the embodiment shown in FIG. 23 with the needle assembly inserted therein.

The syringe 310 is comprised of a hollow body portion 312 which has a closed end 320 and an open end 324 surrounded by a grip ring 326. The hollow body portion 312 preferably has an oval cross-section. The closed end 320 of the hollow body 312 is defined by a cone 314 which includes a truncating plane having an aperture 318. The opposite end of the cone 314 has a tapered portion 317, as shown in FIG. 26, the function of which will be described hereinafter. Proximate the tapered portion 317 is an annular recess 315 which receives collar 346 of the needle assembly 340 and retains it in position during use. A cap receiving sleeve 316 extends from the closed end 320 about the cone 314.

Figure 25:
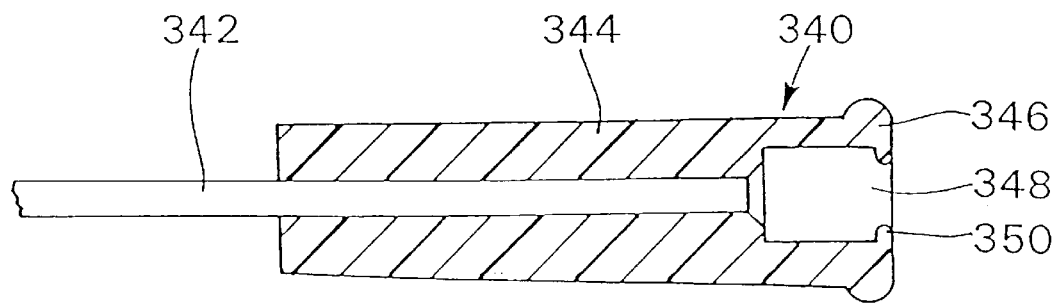
FIG. 25 is a section view taken along the line 25—25 in FIG. 24.
Figure 24:
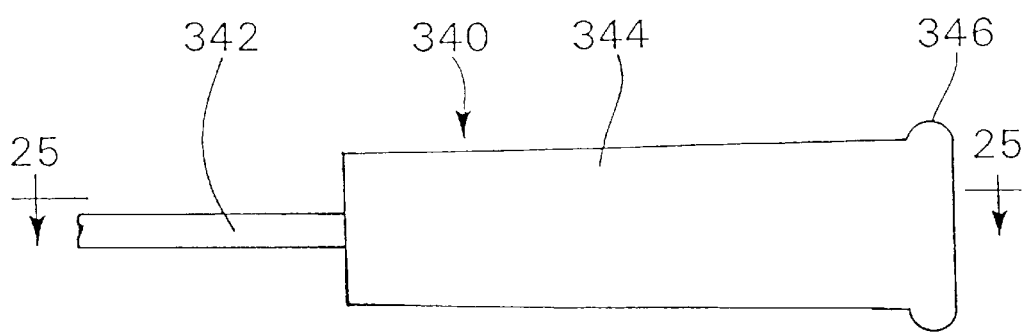
FIG. 24 is an elevation view of an alternate needle assembly for the third embodiment.

The needle assembly 340 is shown in FIGS. 24 and 25. It comprises a needle 342 which is centrally positioned in the conical body 344. The conical body 344 generally complements the interior of the cone 314 of the syringe 310. Adjacent to the body 344 is a resilient collar 346 which retains the needle assembly 340 in position and provides a fluid tight seal against the cone 314. An interior recess 348 of the needle assembly 340 communicates with the hollow needle 342. Along the rear surface of the needle assembly 340 is an inner collar 350 which defines the opening to the cavity 348. The cavity 348 and inner collar 350 are configured to mate with a geometrically configured tip 326 on the plunger assembly 380, as will be described in more detail hereinafter.

Figure 27:
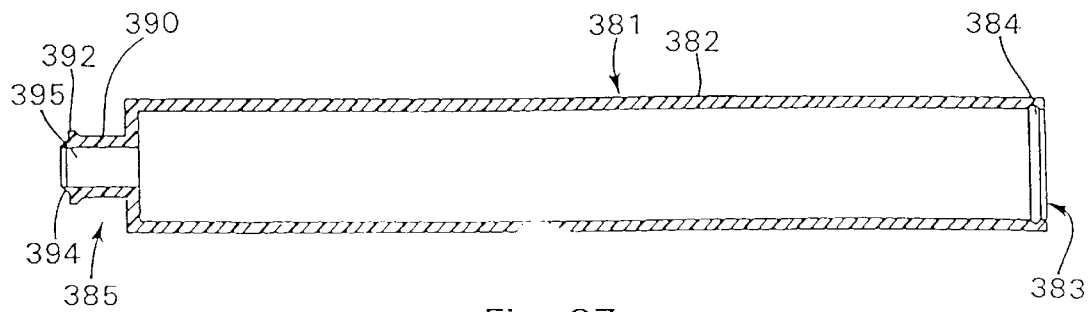
FIG. 27 is a cross-sectional view of the plunger body taken along the line 27—27 in FIG. 23.

The plunger assembly 380 includes a hollow plunger body 381, a sealing member 360, a retraction hub 320, and a plunger pad 400. The plunger body 381 is shown in FIG. 27 and generally comprises a hollow tube 382 which is also preferably oval in cross-section to complement the syringe hollow body 312. One end 383 of the plunger tube 382 is substantially open while the other end 385 has a reduced opening. An annular recess 384 is provided adjacent to the substantially open end 383 to aid in connection of the plunger pad 400 to the plunger tube 382. Hollow shaft 390 extends from the reduced opening end 385 and is axially aligned with the aperture 395. The free end of the shaft 390 has an annular ring 392 extending therefrom. The plunger sealing means 360 is placed on the shaft 390 and maintained in position by the ring 392, see FIG. 29. The plunger body 381 terminates with an annular tapered projection 394 forward of ring 392. The function of the projection 394 will be described in more detail hereinafter.

Figure 28:
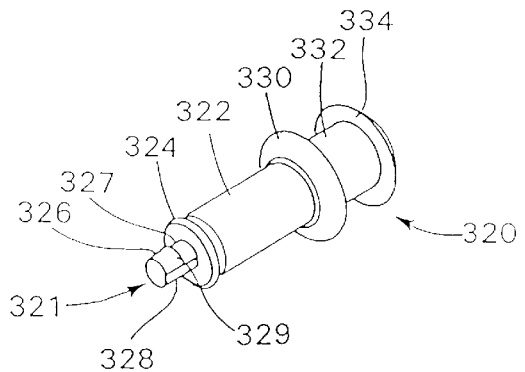
FIG. 28 is an isometric view of the retraction hub of the third embodiment.
Figure 29:
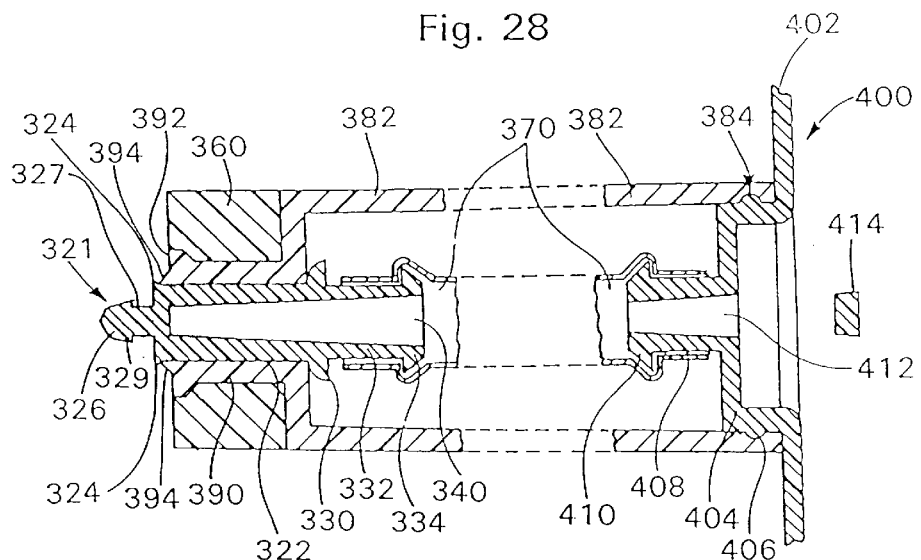
FIG. 29 is an enlarged cross-sectional view for the end portions of the plunger assembly of the embodiment shown in FIG. 23.

Referring to FIGS. 28 and 29, a retraction hub 320 extends through the opening in the shaft 390 and into the hollow tube 382. The retraction hub 320 generally comprises a major tubular body 322 extending between front and rear collars 324 and 330 which maintain the hub 320 in its initial position in the shaft 390 of the plunger body 381. The major tubular body 322 is in sealing engagement with the interior of shaft 390 in this initial position. Extending forward of the front collar 324 is a nipple 321 which includes rod 327 and tapered head 326. The tapered head 326 provides an annular lip 329 between it and the rod 327. The sides of nipple 321 include flattened portions 328. The flattened portions 328 allow fluid to pass by the nipple 321 during depression of the plunger 380. This will be described in more detail hereinafter. Extending rearward from rear collar 330 is a minor tubular body 332 which terminates in a solid retaining ring 334. Alternatively, the retaining ring 334 may be comprised of a plurality of projections.

As shown in FIG. 29, plunger pad 400 is positioned in the substantially open end 383 of the plunger tube 382. The plunger pad 400 includes a force application pad 402 which is attached to the plunger pad body 404. An annular ring 406 extends from the plunger pad body 404 and mates with annular recess 384 in the hollow body 382 to maintain the plunger pad 400 in position. Extending forward from the plunger pad body 404 is a nipple 408 which has retaining ring 410 as its terminate end. Retaining ring 410 retains an end of the elastic member 370 in position. As can be seen in FIG. 29, elastic member 370 extends between the minor tubular body 332 and nipple 408 and is retained in place by retaining rings 334 and 410.

The plunger pad body 404 is preferably provided with an aperture 412 to assist in the manufacture of the plunger assembly 380. With the aperture 412, the elastic member 370 can be attached to both the retraction hub 320 and the plunger pad 400 before insertion into the plunger body 381. The retraction hub 320 can then be placed in the hollow tube 382 and the plunger pad 400 snap fit into its position at the rear of the plunger body 381. By extending a rod member through the aperture 412, the retraction hub 320 can be pushed forward until it snaps into position in the plunger shaft 390. This operation will preload elastic member 370. A recess 340 may also be provided in the rear of the retraction hub 320 to assist in this process.

Since the elastic member 370 extends from the thumb pad 402 to the retraction hub 320, any air or contaminant that could possibly enter through the aperture 412 is prevented from entering the plunger hollow tube 382. This also prevents any contaminated material from escaping out the aperture 412 upon retraction of the needle assembly 340. For example, if blood or the like were to spray off of the needle 342 as it retracted into the plunger hollow tube 382, the elastic member 370 would prevent that material from exiting through the aperture 412.

The aperture 412 may also be configured such that air in the elastic member 370 will cause an audible signal, for example a whistle, as the retraction hub 320 retracts and the elastic member 370 contracts. This will signal the user that the retraction hub 320 has released and retracted.

Once the syringe 308 is assembled as shown in FIG. 30, it is ready for use. The syringe body 312 can be filled in a conventional manner by withdrawing the plunger assembly 380. As in the other embodiments, the elastic member 370 remains in a preloaded condition when the plunger assembly is withdrawn. Once the air has been purged from the syringe 310 in a known manner, the device 308 is ready for injection of the needle 342 into the patient in the usual manner.

As shown in FIG. 31, upon substantial depression of the plunger assembly 380, the tapered head 326 of the retraction hub 320 enters the needle assembly cavity 348. At this time, the lip 329 of the tapered head 326 is forward of and retained by the needle assembly inner collar 350. In this position, the retraction hub 320 has moved as far into the needle assembly 340 as possible, yet the plunger body 381 has not completed its full stroke. As such, continued force on the force application pad 402 will continue to move the plunger body 381 forward. The flat portions 328 of tapered head 326 allow the remaining fluid to pass out through the needle 342 during the final depression of the plunger body 380.

Figure 33:
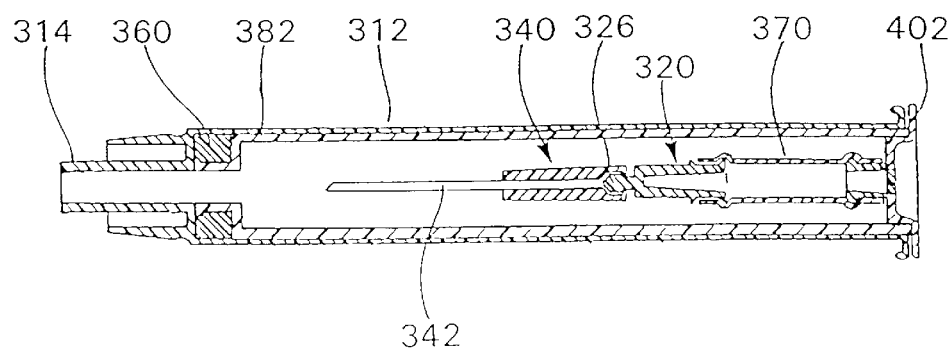
FIG. 33 depicts the syringe of FIG. 23 after it has been used and the needle has been retracted.

Since the retraction hub 320 position is fixed and the plunger body 381 is being forced forward, the forward collar 324 of the retraction hub will move inside of the plunger shaft 390. Because the retraction hub 320 is under the load of the elastic member 370 but no longer retained by the forward collar 324, the load of the elastic member 370 automatically retracts the hub 320 into the plunger hollow tube 382. Through the connection of tapered head 326 and inner collar 350, the needle assembly 340 is also retracted into the hollow plunger tube 382, as shown in FIG. 33. Annular tapered projection 394 on the forward end of the plunger shaft 390 contacts the tapered portion 317 of cone 314 and causes it to spread slightly. This reduces the retaining force of cone 314 on the needle assembly 340 to assist retraction of the needle assembly 340 and allows easier retraction.

Figure 34:
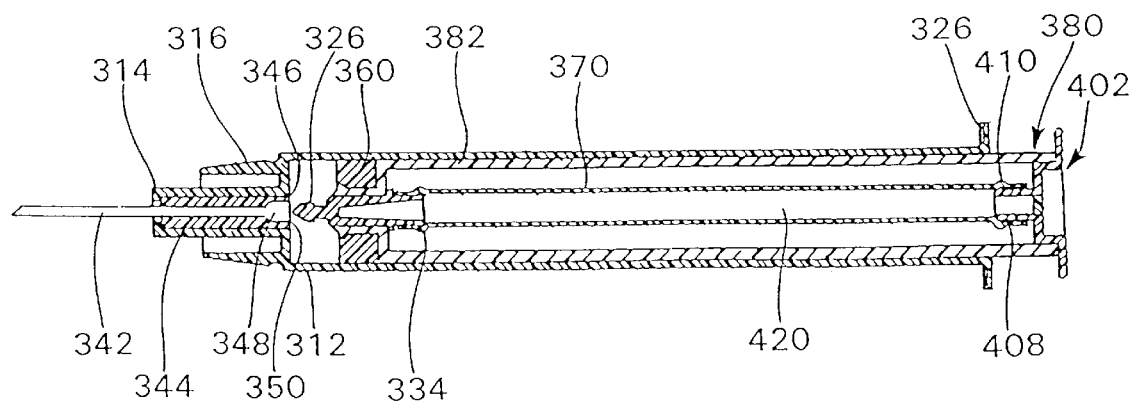
FIG. 34 depicts the syringe of FIG. 23 in an assembled but unused condition with a damper in the elastic member.

As shown in FIG. 34, the aperture 412 also allows a damping material 420 to be placed inside the elastic member 370. Whether or not the damping material 420 is placed in the elastic member 370, a cap 414 may be placed over the aperture 412. A variety of materials, including fluids, may be used in the elastic member 370 to increase the damping effect. In most cases, air contained in the elastic member 370 will provide a sufficient damping effect and may allow some control over the speed of retraction.

Figure 35:
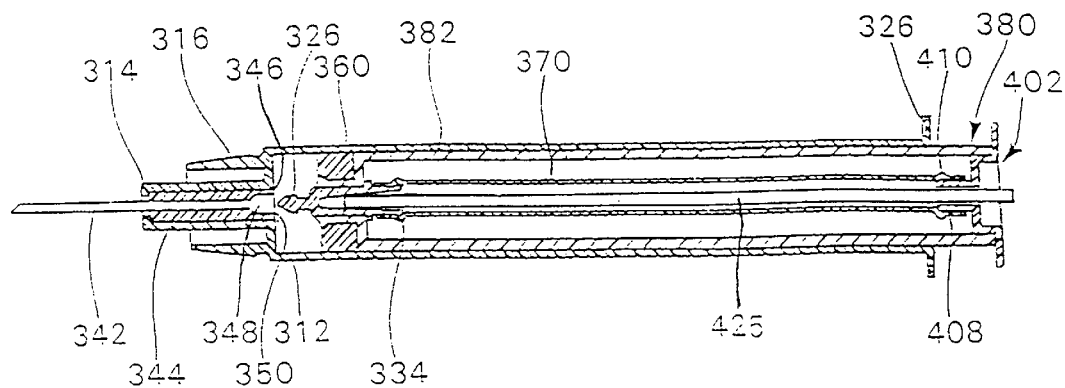
FIG. 35 is an enlarged cross-sectional view for the end portions of the plunger assembly of an alternate embodiment.

Control of retraction may also be enhanced by leaving the aperture 412 open and allowing the user to cover the aperture, for example with their thumb, to regulate the damping effect. The user can slow the escape of the damping material to slow retraction. In an alternate embodiment shown in FIG. 35, a rigid member 425, for example a rod, may extend from the hub 320 and through the aperture 412 to allow the user to manually control the speed of retraction.

Figure 36:
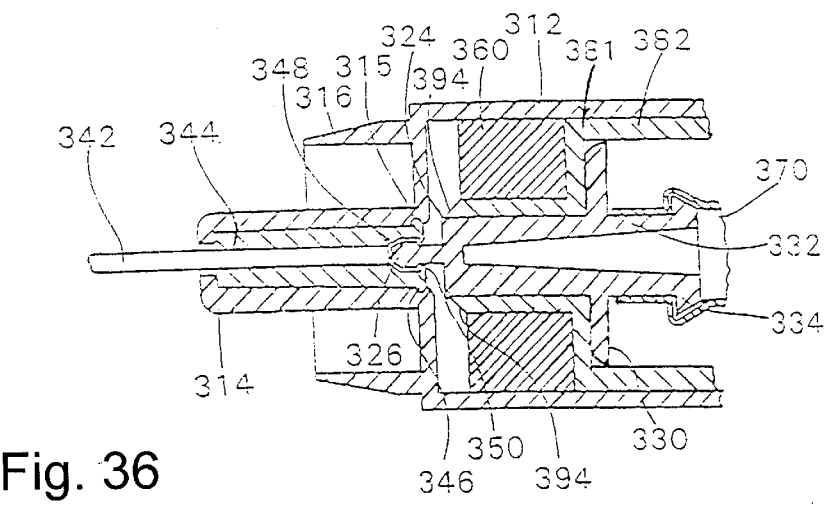
FIG. 36 depicts an expanded cross-sectional view of the forward portion of an alternate embodiment of the syringe.
Figure 37:
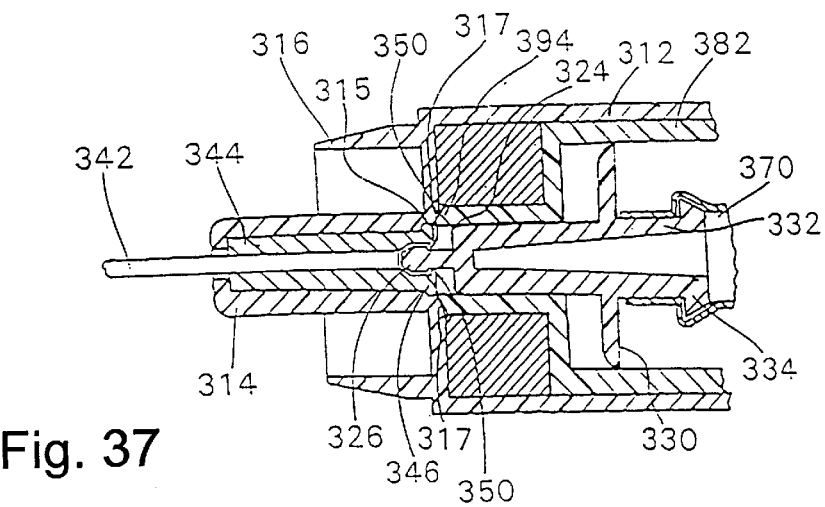
FIG. 37 depicts an expanded cross-sectional view of the forward portion of the syringe shown in FIG. 36.

The rate of retraction may also be controlled by expanding the rear collar 330 of the retraction hub 320 until it contacts the interior of the plunger tube 382, as shown in FIGS. 36 and 37. The friction between the rear collar 330 and the plunger tube 382 slows the rate of retraction. The friction force can be adjusted by varying any of several factors, for example the materials used or the fit between components, to provide a desired rate of retraction.

While the present invention has been described in terms of the preferred embodiments, other variations which are within the scope of the invention as defined in the claims will be apparent to those skilled in the art.

I claim:

1. A disposable, single use syringe comprised of:
   a hollow body which is substantially open at one end and is substantially closed at its other end except for an aperture through which an injection means passes;
   a retractable needle assembly positioned in the hollow body with the injection means passing out through the aperture;
   an elongated plunger which moves in the hollow body and has spaced apart retainer means and means for retracting the needle assembly;
   a preloaded elastic member extending between the spaced apart retainer means; and
   means for automatically releasing the preload on the elastic member upon substantial completion of the injection so that the relaxing elastic member draws the injection means in through the aperture.

2. The syringe of claim 1 wherein the means for retracting the needle assembly includes a first geometric configuration integral with the needle assembly and a second geometric configuration integral with the plunger.

3. The syringe of claim 2 wherein in a first orientation the geometric configurations unite without mating and in a second orientation the geometric configurations mate when united.

4. The syringe of claim 2 wherein the plunger assembly has a stroke of sufficient length to ensure complete mating of the geometric configurations upon discharge of the hollow body.

5. The syringe of claim 2 wherein the second geometric configuration includes at least one passage which allows fluid in the syringe to bypass the second geometric configuration.

6. The syringe of claim 5 wherein the passage allows the fluid in the syringe to bypass the second geometric configuration as the first and second geometric configurations mate.

7. The syringe of claim 1 wherein the means for automatically releasing the preload is a beveled ring.

8. The syringe of claim 1 wherein the needle assembly has a sealing ring which establishes a fluid tight seal against the interior of the hollow body.

9. The syringe of claim 1 wherein the needle assembly is formed as a unitary molding of synthetic material.

10. The syringe of claim 1 wherein the plunger includes a hollow tube.

11. The syringe of claim 10 wherein the means for retracting the needle assembly includes a first geometric configuration integral with the needle assembly and a second geometric configuration integral with the plunger.

12. The syringe of claim 11 wherein the plunger assembly includes a retraction hub and the second geometric configuration is integral therewith.

13. The syringe of claim 12 wherein the needle assembly is withdrawn into the hollow tube.

14. The syringe of claim 12 wherein the retraction hub includes a retention means that maintains the retention hub in the plunger assembly prior to retraction thereof.

15. The syringe of claim 14 wherein the retention means includes a pair of spaced apart collars extending from the retraction hub.

16. The syringe of claim 12 wherein the retraction hub includes a portion which contacts an inside surface of the hollow tube and creates a damping force as the retraction hub is retracted.

17. The syringe of claim 1 wherein the elastic member is a hollow tube.

18. The syringe of claim 17 wherein the elastic member contains a damping material.

19. The syringe of claim 17 wherein the plunger assembly is configured to provide an audible signal as the needle assembly is retracted.

20. The syringe of claim 1 wherein the hollow body has a substantially oval cross-section.

21. The syringe of claim 1 wherein each retainer means includes at least one projection which deforms a portion of the elastic member to retain it in position.

22. The syringe of claim 1 wherein a tapered portion on the plunger assembly contacts the hollow body proximate to the closed end, urges it outwardly, and assists release of the needle assembly from the hollow body.

23. The syringe of claim 1 wherein the plunger includes a hollow integral shaft and a retractable retraction hub which is within and in sealing engagement with the integral shaft prior to retraction thereof.

24. A disposable, single use syringe comprised of:
   a hollow body which is substantially open at one end and is substantially closed at its other end except for an aperture through which an injection means passes;

a needle assembly, having the injection means extending from a first side and a geometric configuration at an opposite second side, is positioned in the hollow body with the injection means passing through the aperture;

an elongated plunger which moves in the hollow body, and has spaced apart retainer means and a complementary geometric configuration at a first end thereof which mates with the needle assembly geometric configuration;

a preloaded elastic member extending between the spaced apart retainer means; and means for automatically releasing the preload on the elastic member upon substantial mating of the geometric configurations so that the relaxing elastic member draws the injection means in through the aperture.

25. The syringe of claim 24 wherein in a first orientation the geometric configurations are unitable without mating and in a second orientation the geometric configurations mate when united.

26. The syringe of claim 25 wherein the substantially open end of the hollow body has a grip ring integral therewith, which grip ring has an integral stop and wherein the means for automatically releasing the preload on the elastic member includes a beveled ring to which an end of the elastic member is attached, whereby pinching of the beveled ring between the stop and a portion of the plunger causes the beveled ring to automatically release from the retainer means.

27. The syringe of claim 24 wherein the elongated plunger has a body portion which includes four ribs integrally formed in a substantially cross shape.

28. The syringe of claim 27 wherein the body is further characterized by a stopper projecting from an inside surface of the body adjacent the substantially closed end.

29. The syringe of claim 28 wherein a plunger rib has a notch defined therein adjacent to the geometric configuration end and of sufficient size to allow the stopper to pass therethrough such that the hollow body may be rotated relative to the plunger.

30. The syringe of claim 29 wherein an abutment is formed between two adjacent ribs.

31. The syringe of claim 30 wherein the plunger is initially aligned within the hollow body such that the abutment contacts the stopper.

32. The syringe of claim 24 wherein one geometric configuration is a collapsible arrow head and the other geometric configuration is a complementary cavity.

33. The syringe of claim 24 wherein the needle assembly has a sealing ring which establishes a fluid tight seal against the interior of the hollow body.

34. The syringe of claim 24 wherein the needle assembly is formed as a unitary molding of synthetic material.

35. The syringe of claim 24 wherein the plunger includes a hollow tube.

36. The syringe of claim 35 wherein the plunger assembly includes a retraction hub and the second geometric configuration is integral therewith.

37. The syringe of claim 36 wherein the needle assembly is withdrawn into the hollow tube.

38. The syringe of claim 36 wherein the retraction hub includes a retention means that maintains the retention hub in the plunger assembly prior to retraction thereof.

39. The syringe of claim 38 wherein the retention means includes a pair of spaced apart collars extending from the retraction hub.

40. The syringe of claim 36 wherein the retraction hub includes a portion which contacts an inside surface of the hollow tube and creates a damping force as the retraction hub is retracted.

41. The syringe of claim 24 wherein the elastic member is a hollow tube.

42. The syringe of claim 41 wherein the elastic member contains a damping material.

43. The syringe of claim 41 wherein the plunger assembly is configured to provide an audible signal as the needle assembly is retracted.

44. The syringe of claim 24 wherein the hollow body has a substantially oval cross-section.

45. The syringe of claim 24 wherein each retainer means includes at least one projection which deforms a portion of the elastic member to retain it in position.

46. The syringe of claim 24 wherein the second geometric configuration includes at least one passage which allows fluid in the syringe to bypass the second geometric configuration.

47. The syringe of claim 46 wherein the passage allows the fluid in the syringe to bypass the second geometric configuration as the first and second geometric configurations mate.

48. The syringe of claim 24 wherein a tapered portion on the plunger assembly contacts the hollow body proximate to the closed end, urges it outwardly, and assists release of the needle assembly from the hollow body.

49. The syringe of claim 24 wherein the plunger includes a hollow integral shaft and a retractable retraction hub which is within and in sealing engagement with the integral shaft prior to retraction thereof.

* * * * *

UNITED STATES PATENT AND TRADEMARK OFFICE
CERTIFICATE OF CORRECTION

PATENT NO : 6,050,977
DATED : April 18, 2000
INVENTOR(S) : Robert D. Adams

It is certified that error appears in the above-identified patent and that said Letters Patent are hereby corrected as shown below:

On the face page, under "Related U.S. Application Data", insert --, which claims priority from U.S. Patent Application No. 08/749,997, Nov. 15, 1996-- after "Nov. 14, 1997".

column 1, line 3, insert --, which claims priority from U.S. Patent Application No. 08/749,997, filed November 15, 1996, now U.S. Patent No. 5,693,023-- after "abandoned".

Signed and Sealed this

First Day of May, 2001

Attest:

NICHOLAS P. GODICI

*Attesting Officer*  *Acting Director of the United States Patent and Trademark Office*